United States Patent [19]

Chang

[11] Patent Number: 5,160,260
[45] Date of Patent: Nov. 3, 1992

[54] ESTHETIC BRACKET PROTECTOR

[76] Inventor: Cheng-Tsung Chang, No. 21-2, Lane 51, Po-ai Street, Tamsui Town, Taipei, Taiwan

[21] Appl. No.: 775,697

[22] Filed: Oct. 10, 1991

[51] Int. Cl.⁵ .............................................. A61C 3/00
[52] U.S. Cl. ........................................... 433/8; 433/2; 433/22
[58] Field of Search ................. 433/2, 6, 8, 11, 22, 433/13

[56] References Cited

U.S. PATENT DOCUMENTS

| | | | |
|---|---|---|---|
| 3,505,736 | 4/1970 | Brader et al. | 433/22 |
| 4,559,013 | 12/1985 | Amstutz et al. | 433/22 |
| 4,609,348 | 9/1986 | Rowland | 433/2 |
| 4,913,654 | 4/1990 | Morgan et al. | 433/8 |
| 5,037,296 | 8/1991 | Karwoski | 433/8 |

Primary Examiner—Gene Mancene
Assistant Examiner—Cindy A. Cherichetti

[57] ABSTRACT

A new esthetic bracket protector is formed of a silicone material and can be placed over the orthodontic bracket to achieve the esthetic purpose. The protector is round-shaped, is hollow in the interior and has a covering. There is a hole in each side for the main wire to pass through and there is a slit from each hole to the base of the covering. In this manner, the protector may be easily pressed over the bracket and wire. It covers the bracket, prevents mucosal ulceration and caries and provides an esthetic appearance.

1 Claim, 2 Drawing Sheets

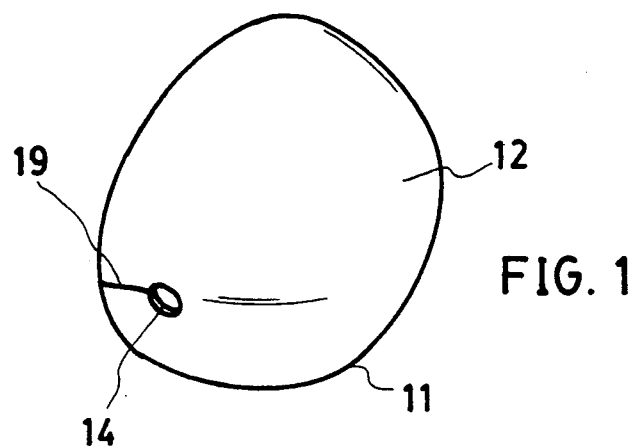
FIG. 1
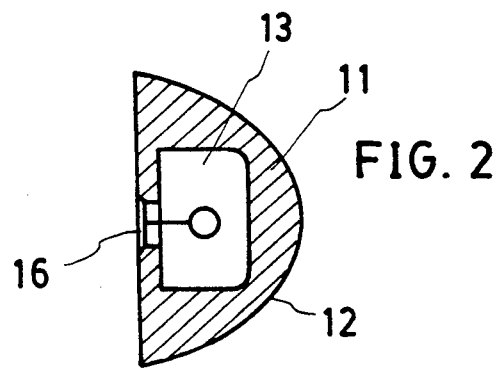
FIG. 2
FIG. 3
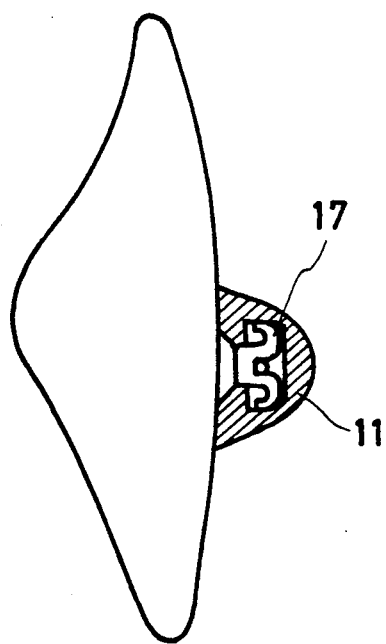

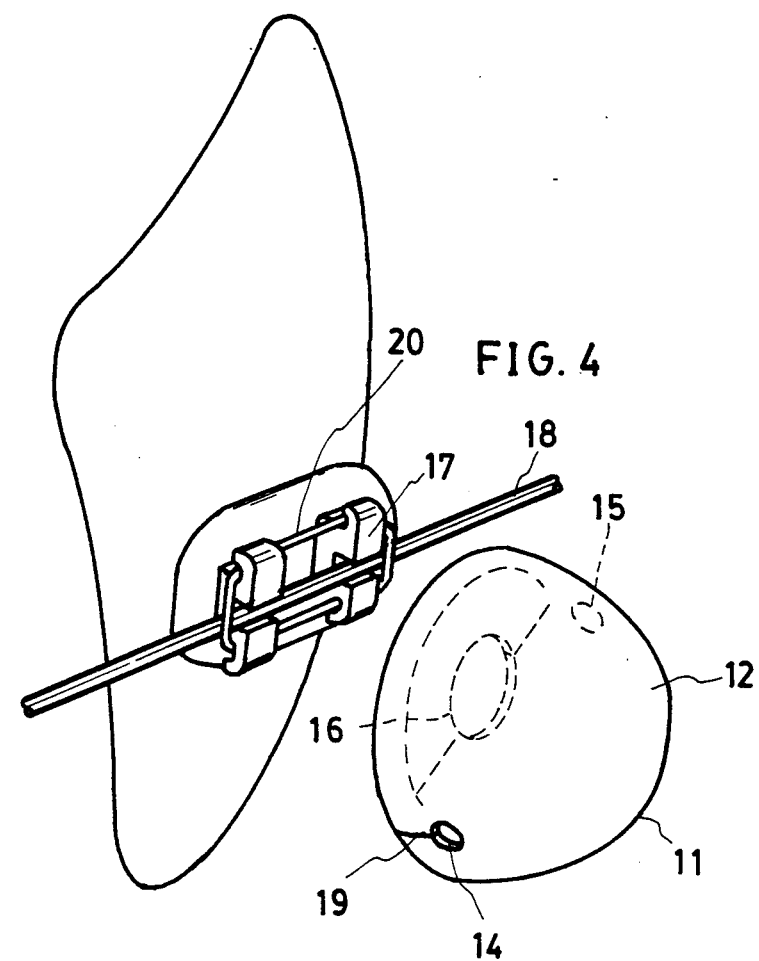
FIG. 4
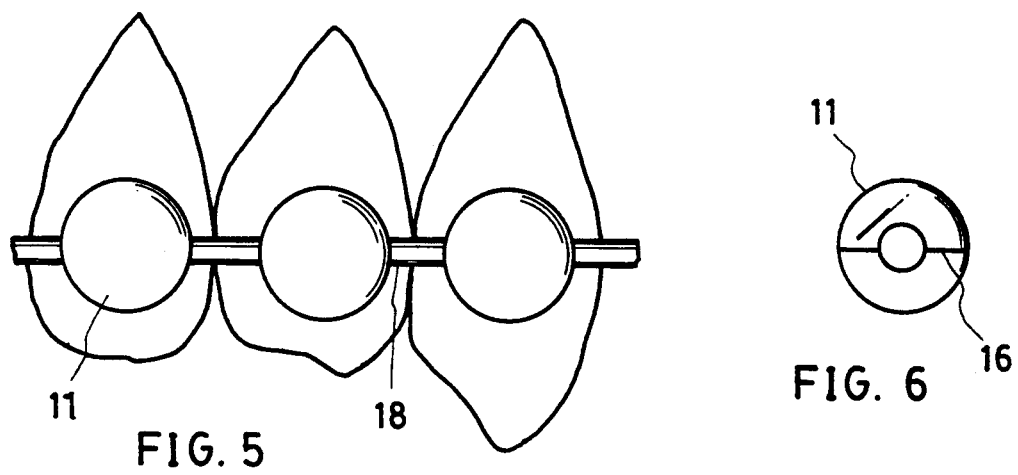
FIG. 5
FIG. 6

ESTHETIC BRACKET PROTECTOR

BACKGROUND OF THE INVENTION

This invention is a newly designed esthetic bracket protector, especially referred to as a protector which is innovative and functional; can be locked in the orthodontic appliance to get a better appearance and prevent mucosal ulceration and caries.

Malocclusion is an ordinary dental defect, and must be corrected by orthodontic wires and brackets to align the malpositioned teeth into a proper position. The appearance of the teeth is affected by using the orthodontic appliance to correct the defect because the brackets and wires have to be attached over the tooth surfaces. Sometimes they even cause mucosal ulceration and caries. The inconvenience caused by the orthodontic appliance has not been eliminated yet.

SUMMARY OF THE INVENTION

Therefore, an object of this invention is to resolve the above problems and to provide an esthetic bracket protector.

Another object of this invention is to provide a protector which is novel and functional and can be fitted over the bracket of the orthodontic appliance.

In accordance with the invention, the main wire is locked in the wire hole and is held on the bracket in situ, so the patient can have a better appearance and prevent mucosal ulceration and caries.

The features of the bracket protector of this invention will be described below:

1. It can be placed over the orthodontic appliance;
2. It permits to achieve a better appearance;
3. It permits to hold the wire tight and to make it more effective;
4. It permits to cover the orthodontic appliance to to prevent mucosal ulceration and caries;
5. Fluoride can be applied to prevent caries;
6. It is formed by a thin silicone material with good elasticity to hold the wire tight and make it more effective;
7. It has a round periphery and hollow interior for easy access.

BRIEF DESCRIPTION OF THE DRAWINGS

FIG. 1 is a perspective view of the protector of this invention.

FIG. 2 is a sectional view of the protector of this invention.

FIG. 3 is a sectional view of the protector of this invention placed over the bracket.

FIG. 4 is a schematic diagram of the protector of this invention before being placed over the bracket.

FIG. 5 illustrates an outline of the protector when it is placed over the bracket and wire.

FIG. 6 is a rear view of the configuration of the protector of this invention.

DETAILED DESCRIPTION OF THE PREFERRED EMBODIMENT

As shown in the figures the esthetic bracket protector has a round periphery 12, a hollow interior 13 and a covering 11. On two opposite sides the covering 11 there are holes 14, 15 for the wire to be locked in. There is another opening 16 on the inner surface of the covering 11 and a slit 19 which communicates the main holes 14, 15 and the opening 16. The protector itself is formed by a thin silicone material, and has good elasticity. As shown in FIG. 4 the opening 16 and the slit 19 on the inner surface of the covering 11 provide ready access for the covering 11 to be placed over the bracket. The covering 11 is placed through the opening 16 and entraps the bracket 17 into the hollow interior 13. In this manner, the covering 11 can hold the bracket 17 tight. The main wire 18 is connected with brackets 17 by ligature wire 20. The main wire 18 can also be placed into the holes 14 through the slit 19 on the inner surface of the covering 11. Thus the bracket is entirely covered by the covering 11 to achieve the esthetic purpose and prevent the mucosal ulceration.

Fluoride can be applied in the inner surface 13 of the covering 11 to prevent caries whenever it is necessary. The covering 11 formed by thin silicone material has good elasticity so that the brackets 17 can be tightly held. The dentist can place the covering over the bracket and use a button or other kind of appliance on either the labial or the lingual surface as a tight wrapping.

The structure itself is very simple, but a better appearance, mucosal ulceration caries prevention and better wire-holding can be achieved by the round periphery and hollow interior.

I claim:

1. A bracket protector to be placed over an orthodontic bracket, said bracket having a wire, said protector consisting of a round-shaped hollow body, a covering, said covering having two orifices and two slits formed in two opposite sides of said covering said covering having an inner surface and an opening formed in said inner surface, the improvement which comprises:

each said orifice having a slit extending from each said orifice to a base of said covering, each said slit communicating each said orifice formed in each side of said covering and said opening formed in said inner surface of said covering, whereby upon a pressing of said protector on said bracket, said wire will be locked in said two orifices of said covering through said two slits for securing said protector on said bracket.

* * * * *